United States Patent
Laredo (10) Patent No.: US 8,153,703 B2
(45) Date of Patent: Apr. 10, 2012

(54) UV/VISIBLE LIGHT ABSORBERS FOR OPHTHALMIC LENS MATERIALS

(75) Inventor: Walter R. Laredo, Fort Worth, TX (US)

(73) Assignee: Novartis AG, Basel (CH)

( * ) Notice: Subject to any disclaimer, the term of this patent is extended or adjusted under 35 U.S.C. 154(b) by 238 days.

(21) Appl. No.: 12/611,539

(22) Filed: Nov. 3, 2009

(65) Prior Publication Data

US 2010/0113641 A1 May 6, 2010

Related U.S. Application Data

(60) Provisional application No. 61/111,204, filed on Nov. 4, 2008.

(51) Int. Cl.
*G02B 1/04* (2006.01)
*G02C 7/04* (2006.01)
*C08L 39/04* (2006.01)
*C08F 271/02* (2006.01)
*C08F 26/06* (2006.01)
*C08F 226/06* (2006.01)
*C07D 249/18* (2006.01)
*C07D 249/20* (2006.01)

(52) U.S. Cl. ........ 523/107; 523/106; 525/204; 525/259; 525/281; 526/259; 526/261; 526/263; 548/255; 548/257; 351/160 R; 351/163

(58) Field of Classification Search .................. 523/107, 523/106; 351/163, 160 R; 525/204, 259, 525/281; 526/259, 261, 263; 548/255, 257
See application file for complete search history.

(56) References Cited

U.S. PATENT DOCUMENTS

| | | | |
|---|---|---|---|
| 3,880,875 | A | 4/1975 | Strobel et al. |
| 4,310,650 | A | 1/1982 | Gupta et al. |
| 4,390,676 | A | 6/1983 | Loshaek |
| 4,528,311 | A | 7/1985 | Beard et al. |
| 4,611,061 | A | 9/1986 | Beard et al. |
| 4,716,234 | A | 12/1987 | Dunks et al. |
| 4,795,461 | A | 1/1989 | Lindqvist et al. |
| 4,803,254 | A | 2/1989 | Dunks et al. |
| 5,147,902 | A | 9/1992 | Ichikawa et al. |
| 5,235,358 | A | 8/1993 | Mutzhas et al. |
| 5,290,892 | A | 3/1994 | Namdaran et al. |
| 5,331,073 | A | 7/1994 | Weinschenk, III et al. |
| 5,470,932 | A | 11/1995 | Jinkerson |
| 5,487,885 | A | 1/1996 | Sovak et al. |
| 5,528,322 | A | 6/1996 | Jinkerson |
| 5,543,504 | A | 8/1996 | Jinkerson |
| 5,637,726 | A | 6/1997 | Collins et al. |
| 5,662,707 | A | 9/1997 | Jinkerson |
| 5,693,095 | A | 12/1997 | Freeman et al. |

(Continued)

FOREIGN PATENT DOCUMENTS

| | | |
|---|---|---|
| CN | 1727338 | 2/2006 |
| EP | 0282294 A2 | 9/1988 |
| EP | 0283166 A1 | 9/1988 |
| EP | 0455058 A2 | 11/1991 |

(Continued)

OTHER PUBLICATIONS

Acrysof Natural Product Monograph, Alcon Laboratories, Inc. 2004.

(Continued)

*Primary Examiner* — Michael Pepitone
(74) *Attorney, Agent, or Firm* — Patrick M. Ryan (57) ABSTRACT

Benzotriazole UV/Visible light-absorbing monomers are disclosed. The UV/Vis absorbers are particularly suitable for use in intraocular lens materials.

19 Claims, 6 Drawing Sheets

UV/Vis Spectra Of UV Absorbers in CHCl3, 10 mm Path Length

U.S. PATENT DOCUMENTS

| | | | |
|---|---|---|---|
| 5,741,924 A | 4/1998 | Sovak et al. | |
| 5,861,031 A | 1/1999 | Namdaran et al. | |
| 6,015,874 A | 1/2000 | Hiratani | |
| 6,153,760 A * | 11/2000 | Kunzler | 548/259 |
| 6,166,218 A | 12/2000 | Ravichandran et al. | |
| 6,242,551 B1 | 6/2001 | Tsuzuki et al. | |
| 6,244,707 B1 | 6/2001 | Faubl | |
| 6,310,215 B1 | 10/2001 | Iwamoto | |
| 6,320,008 B2 | 11/2001 | Tsuzuki et al. | |
| 6,326,448 B1 | 12/2001 | Ojio et al. | |
| 6,528,602 B1 | 3/2003 | Freeman et al. | |
| 6,703,466 B1 | 3/2004 | Karakelle et al. | |
| 6,806,337 B2 | 10/2004 | Schleuter et al. | |
| 6,846,897 B2 | 1/2005 | Salamone et al. | |
| 6,852,793 B2 | 2/2005 | Salamone et al. | |
| 6,872,793 B1 | 3/2005 | Schlueter | |
| 6,878,792 B2 | 4/2005 | Ichinohe | |
| 6,918,931 B2 | 7/2005 | Lai et al. | |
| 7,037,954 B2 | 5/2006 | Baba et al. | |
| 7,067,602 B2 | 6/2006 | Benz et al. | |
| 7,098,283 B2 | 8/2006 | Lai | |
| 7,101,949 B2 | 9/2006 | Salamone et al. | |
| 7,119,210 B2 | 10/2006 | Schlueter | |
| 7,278,737 B2 | 10/2007 | Mainster et al. | |
| 7,326,423 B2 | 2/2008 | Pearson et al. | |
| 7,396,942 B2 | 7/2008 | Schlueter | |
| 2002/0042653 A1 | 4/2002 | Copeland et al. | |
| 2003/0223954 A1 | 12/2003 | Ruscio et al. | |
| 2003/0236375 A1 | 12/2003 | Salamone et al. | |
| 2005/0054797 A1 | 3/2005 | Lai | |
| 2005/0054803 A1 | 3/2005 | Lai et al. | |
| 2005/0055090 A1 | 3/2005 | Lai et al. | |
| 2005/0055091 A1 | 3/2005 | Lai et al. | |
| 2005/0143812 A1 | 6/2005 | Paul et al. | |
| 2005/0222427 A1 | 10/2005 | Sharpless et al. | |
| 2005/0243272 A1 | 11/2005 | Mainster et al. | |
| 2005/0283234 A1 | 12/2005 | Zhou et al. | |
| 2006/0020337 A1 | 1/2006 | Lai et al. | |
| 2006/0020338 A1 | 1/2006 | Lai et al. | |
| 2006/0020340 A1 | 1/2006 | Lai et al. | |
| 2006/0041038 A1 | 2/2006 | Xia | |
| 2006/0096044 A1 | 5/2006 | Miki et al. | |
| 2006/0115516 A1 | 6/2006 | Pearson et al. | |
| 2006/0197067 A1 | 9/2006 | Xia et al. | |
| 2006/0241263 A1 | 10/2006 | Lai | |
| 2006/0241264 A1 | 10/2006 | Lai | |
| 2006/0252844 A1 | 11/2006 | Mentak | |
| 2006/0252850 A1 | 11/2006 | Jani et al. | |
| 2007/0092830 A1 | 4/2007 | Lai et al. | |
| 2007/0092831 A1 | 4/2007 | Lai et al. | |
| 2007/0113587 A1 | 5/2007 | Van Gemert | |
| 2008/0090937 A1 | 4/2008 | Jinkerson et al. | |
| 2008/0200982 A1* | 8/2008 | Your | 623/6.37 |
| 2008/0242818 A1 | 10/2008 | Benz et al. | |
| 2008/0266519 A1 | 10/2008 | Schlueter | |
| 2009/0043007 A1 | 2/2009 | Weinschenk, III et al. | |
| 2009/0043105 A1 | 2/2009 | Weinschenk, III et al. | |

FOREIGN PATENT DOCUMENTS

| | | |
|---|---|---|
| EP | 0488145 A2 | 6/1992 |
| EP | 0989124 B1 | 3/2000 |
| EP | 0913713 B1 | 12/2002 |
| EP | 1033590 B1 | 5/2008 |
| GB | 1356434 | 6/1974 |
| JP | 61054982 | 3/1986 |
| JP | 63188669 | 8/1988 |
| JP | 63235375 | 9/1988 |
| JP | 1299560 | 4/1989 |
| JP | 1250944 | 10/1989 |
| JP | 3152271 | 6/1991 |
| JP | 4193869 | 7/1992 |
| JP | 6088064 | 3/1994 |
| JP | 6088065 | 3/1994 |
| JP | 08176139 | 7/1996 |
| JP | 08-208628 | 8/1996 |
| JP | 2001252346 | 9/2001 |
| JP | 2002046358 | 2/2002 |
| JP | 2004137395 | 5/2004 |
| JP | 2005053058 | 3/2005 |
| JP | 2009-013148 | 1/2009 |
| JP | 2009013148 | 1/2009 |
| WO | WO9414410 A1 | 7/1994 |
| WO | WO9424112 A1 | 10/1994 |
| WO | WO9830900 A2 | 7/1998 |
| WO | WO0004848 A1 | 2/2000 |
| WO | WO0034804 A1 | 6/2000 |
| WO | WO03087177 A2 | 10/2003 |
| WO | WO03087178 A1 | 10/2003 |
| WO | WO2006057824 A2 | 6/2006 |
| WO | WO2006119304 A1 | 11/2006 |
| WO | WO2006119328 A1 | 11/2006 |
| WO | WO2006121876 | 11/2006 |
| WO | WO2006121876 A2 | 11/2006 |
| WO | WO2007050394 A2 | 5/2007 |
| WO | WO2007050395 A2 | 5/2007 |
| WO | WO2007147599 | 12/2007 |
| WO | WO2008109624 A2 | 9/2008 |

OTHER PUBLICATIONS

Braunstein, et al., "A Blue-Blocking Intraocular Lens Should be Used in Cataract Surgery," Arch. Ophthalmology, 2005, pp. 547-549, vol. 123.

Hawker, et al., "The Convergence of Synthetic Organic and Polymer Chemistries," Science, 2005, pp. 1200-1205, vol. 309.

Kador, et al., "Irreversible Aldose Reductase Inhibitors," Enzymology and Molecular Biology of Carbonyl Metabolism, 1987, pp. 353-365.

Kador, et al., "Identification of an Aldose Reductase Inhibitor Site by Affinity Labeling," Biorganic & Medicinal Chemistry, 1995, pp. 1313-1324, vol. 3, No. 10.

Kolb, et al., "Click Chemistry: Diverse Chemical Function From a Few Good Reactions," Angew Chem. Int. Ed., 2001, pp. 2004-2021, vol. 40.

Ladmiral, et al., "Synthesis of Neoglygopolymers by a Combination of "Click Chemistry" and Living Radical Polymerization," J. American Chemical Society, 2006, pp. 4823-4830, vol. 128.

Mainster, et al., "The Spectra, Classification, and Rationale of Ultraviolet-Protective Intraocular Lenses," American J. of Ophthalmology, 1986, pp. 727-732, vol. 102.

Mainster, et al., "How Much Blue Light Should an IOL Transmit?" British J. of Ophthalmology, 2003, pp. 1523-1529, vol. 87.

Mainster, et al., "Intraocular Lenses Should Block UV Radiation and Violet But Not Blue Light," Arch. Ophthalmology, 2005, pp. 550-555, vol. 123.

Mainster, et al., "Violet and Blue Light Blocking Intraocular Lenses: Photoprotection Versus Photoreception," British J. of Ophthalmology, 2006, pp. 784-792, vol. 90.

PCT International Search Report for corresponding PCT/US2007/081204 with mailing date Jul. 3, 2008.

PCT Written Opinion for corresponding PCT/US2007/081204 with mailing date Jul. 3, 2008.

Riker, Jochen, et al., "Ultraviolet Stabilizers of the 2-(Hydroxyphenyl)benzotriazole Class. Influence of Substituents on Structure and Spectra," J. Phys. Chem. 1992, pp. 10225-10234, vol. 96.

Rostovtsev, et al., "A Stepwise Husigen Cycloaddition Process: Copper (I)-Catalyzed Regioselective "Ligation" of Azides and Terminal Alkynes," Angew Chem. Int. Ed., 2002, pp. 2596-2599, vol. 41(14).

Takakis, et al., "Preparation of Benzofuroxans and Benzofurazans of 2,3,4,5-Tetrahydrobenzo[b][1.4]dioxocin and Related Compounds," J. Heterocyclic Chem., 1990, pp. 177-181, vol. 27.

Thibault, et al., "Combination of LFRP and Click Chemistry for Orthogonal Modification of Well-Defined Terpolymers," Polymer Preprints, 2005, p. 10, vol. 46(1).

Van De Kraats, et al., "Sharp Cutoff Filters in Intraocular Lenses Optimize the Balance Between Light Reception and Light Protection," J. Cataract Refractive Surgery, 2007, pp. 879-887, vol. 33.

Vogt, et al., "An Efficient Route to Macromonomers via ATRP and Click Chemistry," Macromolecules, 2006, pp. 5286-5292, vol. 39.

Zhao, et al., "The Effect of Chromatic Dispersion on Pseudophakic Optimal Performance," British J. of Ophthalmology, 2007, pp. 1225-1229, vol. 91.

* cited by examiner

UV/Vis Spectra Of 1 mm Thick Test Sample Of
Example 17A (N=1), Immersed In PBS And Irradiated
In Quartz Cuvette

Fig. 2B

UV/Vis Spectra Of 1 mm Thick Test Sample Of
Example 17B (N=1), Immersed In PBS And Irradiated
In Quartz Cuvette

Fig. 2C

UV/Vis Spectra Of 1 mm Thick Test Sample Of
Example 17C (N=1), Immersed In PBS And Irradiated
In Quartz Cuvette

Fig. 2D

UV/Vis Spectra Of 1 mm Thick Test Sample Of
Example 17D (N=1), Immersed In PBS And Irradiated
In Quartz Cuvette

Fig. 2E

UV/Vis Spectra Of 1 mm Thick Test Sample Of Example 17E (N=1), Immersed In PBS And Irradiated In Quartz Cuvette

Fig. 2F

UV/Vis Spectra Of 1 mm Thick Test Sample Of Example 17F (N=1), Immersed In PBS And Irradiated In Quartz Cuvette

Fig. 2G

UV/Vis Spectra Of 1 mm Thick Test Sample Of
Example 17G (N=1), Immersed In PBS And Irradiated
In Quartz Cuvette

Fig. 2H

UV/Vis Spectra Of 1 mm Thick Test Sample Of
Example 17H (N=1), Immersed In PBS And Irradiated
In Quartz Cuvette

Fig. 2I

UV/Vis Spectra Of 1 mm Thick Test Sample Of
Example 17I (N=3), Immersed In PBS And Irradiated
In Quartz Cuvette

Fig. 2J

UV/Vis Spectra Of 1 mm Thick Test Sample Of
Example 17J (N=3), Immersed In PBS And Irradiated
In Quartz Cuvette

UV/VISIBLE LIGHT ABSORBERS FOR OPHTHALMIC LENS MATERIALS

CROSS-REFERENCE TO RELATED APPLICATIONS

This application claims priority under 35 U.S.C. §119 to U.S. Provisional Patent Application No. 61/111,204, filed Nov. 4, 2008, the entire contents of which are incorporated herein by reference.

FIELD OF THE INVENTION

This invention is directed to ultraviolet/visible light absorbers. In particular, this invention relates to novel benzotriazole monomers especially suitable for use in implantable ophthalmic lens materials.

BACKGROUND OF THE INVENTION

Many ultraviolet and visible light absorbers are known as ingredients for polymeric materials used to make ophthalmic lenses. Such absorbers are preferably covalently bound to the polymeric network of the lens material instead of simply physically entrapped in the material to prevent them from migrating, phase separating or leaching out of the lens material. Such stability is particularly important for implantable ophthalmic lenses where the leaching of the absorber may present both toxicological issues and lead to the loss of UV/visible blocking activity in the implant.

Numerous copolymerizable benzatriazole, benzophenone and triazine absorbers are known. Most of these compounds are known as UV absorbers, though some may be known to also absorb some portion of visible light. Many absorbers contain conventional olefinic polymerizable groups, such as methacrylate, acrylate, methacrylamide, acrylamide or styrene groups. Copolymerization with other ingredients in the lens materials, typically with a radical initiator, incorporates the absorbers into the resulting polymer chain. Incorporation of additional functional groups on an absorber may influence one or more of the absorber's light-absorbing properties, solubility or reactivity. If the absorber does not have sufficient solubility in the remainder of the ophthalmic lens material ingredients or polymeric lens material, the absorber may coalesce into domains that could interact with light and result in decreased optical clarity of the lens.

Examples of polymeric ophthalmic lens materials that incorporate UV absorbers can be found in U.S. Pat. Nos. 5,290,892; 5,331,073 and 5,693,095.

SUMMARY OF THE INVENTION

The present invention provides benzotriazole light absorbing monomers that absorb both ultraviolet light and a portion of visible light ("UV/Vis absorbers"). These absorbers are suitable for use in ophthalmic lenses, including contact lenses. They are particularly useful in implantable lenses, such as intraocular lenses (IOLs).

The absorber compounds of the present invention absorb wavelengths of light between 400-450 nm in addition to higher energy UVA rays between 400-320 nm, UVB rays between 320-280 nm, and UVC rays below 280 nm. They contain reactive groups, which allow for covalent attachment of the absorbers to ocular lens materials. Additionally, the absorbers of the present invention can be synthesized in approximately 5 steps from readily available starting materials.

DETAILED DESCRIPTION OF THE INVENTION

Unless indicated otherwise, all ingredient amounts expressed in percentage terms are presented as % w/w.

The UV/Vis absorbers of the present invention are represented by the formula wherein
$R^1$=H, $CH_3$, $CH_2CH_3$, or $CH_2OH$;
$R^2$=$C_1$-$C_4$ alkyl or $C_1$-$C_4$ alkoxy; and
$R^3$=H, $CH_3$, $CH_3O$, F, Cl, Br, I, or $CF_3$.

Preferred UV/Vis absorbers of the present invention are those wherein $R^1$=H or $CH_3$; $R^2$=$C_1$-$C_4$ alkoxy; and $R^3$=H, $CH_3$, $CH_3O$, F, Cl, or $CF_3$.

More preferred absorbers of the present invention are selected from the group consisting of:

2-hydroxy-5-methoxy-3-(5-(trifluoromethyl)-2H-benzo[d][1,2,3]triazol-2-yl)benzyl methacrylate;

3-(5-fluoro-2H-benzo[d][1,2,3]triazol-2-yl)-2-hydroxy-5-methylbenzyl methacrylate;

3-(2H-benzo[d][1,2,3]triazol-2-yl)-2-hydroxy-5-methoxybenzyl methacrylate;

3-(5-chloro-2H-benzo[d][1,2,3]triazol-2-yl)-2-hydroxy-5-methoxybenzyl methacrylate;

2-hydroxy-5-methoxy-3-(5-methoxy-2H-benzo[d][1,2,3]triazol-2-yl)benzyl methacrylate;

2-hydroxy-5-methoxy-3-(5-methyl-2H-benzo[d][1,2,3]triazol-2-yl)benzyl methacrylate; and

2-hydroxy-5-methyl-3-(5-(trifluoromethyl)-2H-benzo[d][1,2,3]triazol-2-yl)benzyl methacrylate.

Most preferred UV/Vis absorbers of the present invention are 2-hydroxy-5-methoxy-3-(5-(trifluoromethyl)-2H-benzo[d][1,2,3]triazol-2-yl)benzyl methacrylate and 3-(5-chloro-2H-benzo[d][1,2,3]triazol-2-yl)-2-hydroxy-5-methoxybenzyl methacrylate.

The synthesis of the UV/Vis absorbers of the present invention is described below.

Step 1: Phenol derivative 1 is synthesized via the hydroxymethylation of p-methoxyphenol as shown below.

Step 1

-continued

In steps 2 and 3, the diazonium salt of a 2-nitroaniline derivative is synthesized and subsequently reacted with 1 to form an azo dye.

In step 4, the azo dye is treated with a reducing agent, such as formamidinesulfinic acid, to form the corresponding benzotriazole compound. The purity of the isolated benzotriazole compound can be enhanced by techniques known in the art, including filtration of excess reducing agent and reducing agent byproducts before addition of protic acids and column chromatography.

In step 5, the benzotriazole from step 4 is esterified to form a "reactive" compound which contains a vinyl group. By "reactive" it is understood that the vinyl group can polymerize to form covalent bonds when reacted with vinyl monomers, co-monomers, macromers, crosslinking agents, and other components typically used in making polymer-based ocular materials, particularly acrylics. The reactive groups are preferably acrylate or methacrylate groups.

The UV/Vis absorbers of the present invention are particularly suitable for use in IOLs. IOL materials will generally contain from 0.1 to 3% (w/w) of a UV/Vis absorber of the present invention. Preferably, IOL materials will contain from 0.2 to 2.5% (w/w) of an absorber of the present invention. Most preferably, IOL materials will contain from 0.3 to 2% (w/w) of an absorber of the present invention. Such device materials are prepared by copolymerizing the absorbers of the present invention with other ingredients, such as device-forming materials, cross-linking agents, and optionally blue-light blocking chromophores.

Many device-forming monomers are known in the art and include both acrylic and silicone-containing monomers among others. See, for example, U.S. Pat. Nos. 7,101,949; 7,067,602; 7,037,954; 6,872,793 6,852,793; 6,846,897; 6,806,337; 6,528,602; and 5,693,095. In the case of IOLs, any known IOL device material is suitable for use in the compositions of the present invention. Preferably, the ophthalmic device materials comprise an acrylic or methacrylic device-forming monomer. More preferably, the device-forming monomers comprise a monomer of formula IV:

where in formula IV:
A is H, CH$_3$, CH$_2$CH$_3$, or CH$_2$OH;
B is (CH$_2$)$_m$ or [O(CH$_2$)$_2$]$_z$;
C is (CH$_2$)$_w$;
m is 2-6;
z is 1-10;
Y is nothing, O, S, or NR', provided that if Y is O, S, or NR', then B is (CH$_2$)$_m$;
R' is H, CH$_3$, C$_n$H$_{2n'+1}$ (n'=1-10), iso-OC$_3$H$_7$, C$_6$H$_5$, or CH$_2$C$_6$H$_5$;
w is 0-6, provided that m+w≧8; and
D is H, C$_1$-C$_4$ alkyl, C$_1$-C$_4$ alkoxy, C$_6$H$_5$, CH$_2$C$_6$H$_5$ or halogen.

Preferred monomers of formula IV are those wherein A is H or CH$_3$, B is (CH$_2$)$_m$, m is 2-5, Y is nothing or O, w is 0-1, and D is H. Most preferred are 2-phenylethyl methacrylate; 4-phenylbutyl methacrylate; 5-phenylpentyl methacrylate; 2-benzyloxyethyl methacrylate; and 3-benzyloxypropyl methacrylate; and their corresponding acrylates.

Monomers of formula IV are known and can be made by known methods. For example, the conjugate alcohol of the desired monomer can be combined in a reaction vessel with methyl methacrylate, tetrabutyl titanate (catalyst), and a polymerization inhibitor such as 4-benzyloxy phenol. The vessel can then be heated to facilitate the reaction and distill off the reaction by-products to drive the reaction to completion. Alternative synthesis schemes involve adding methacrylic acid to the conjugate alcohol and catalyzing with a carbodiimide or mixing the conjugate alcohol with methacryloyl chloride and a base such as pyridine or triethylamine.

Device materials generally comprise a total of at least about 75%, preferably at least about 80%, of device-forming monomers.

In addition to an absorber of the present invention and a device-forming monomer, the device materials of the present invention generally comprise a cross-linking agent. The cross-linking agent used in the device materials of this invention may be any terminally ethylenically unsaturated compound having more than one unsaturated group. Suitable cross-linking agents include, for example: ethylene glycol dimethacrylate; diethylene glycol dimethacrylate; allyl methacrylate; 1,3-propanediol dimethacrylate; 2,3-propanediol dimethacrylate; 1,6-hexanediol dimethacrylate; 1,4-butanediol dimethacrylate; CH$_2$=C(CH$_3$)C(=O)O—(CH$_2$CH$_2$O)$_p$—C(=O)C(CH$_3$)=CH$_2$ where p=1-50; and CH$_2$=C(CH$_3$)C(=O)O(CH$_2$)$_t$O—C(=O)C(CH$_3$)=CH$_2$ where t=3-20; and their corresponding acrylates. A preferred cross-linking monomer is CH$_2$=C(CH$_3$)C(=O)O—(CH$_2$CH$_2$O)$_p$—C(=O)C(CH$_3$)=CH$_2$ where p is such that the number-average molecular weight is about 400, about 600, or about 1000.

Generally, the total amount of the cross-linking component is at least 0.1% by weight and, depending on the identity and concentration of the remaining components and the desired physical properties, can range to about 20% by weight. The preferred concentration range for the cross-linking component is 1-5% for small, hydrophobic compounds with molecular weights typically less than 500 Daltons, and 5-17% (w/w) for larger, hydrophilic compounds with molecular weights typically between 500-5000 Daltons.

Suitable polymerization initiators for device materials containing a UV/Vis absorber of the present invention include thermal initiators and photoinitiators. Preferred thermal initiators include peroxy free-radical initiators, such as t-butyl (peroxy-2-ethyl)hexanoate and di-(tert-butylcyclohexyl)peroxydicarbonate (commercially available as Perkadox® 16 from Akzo Chemicals Inc., Chicago, Ill.). Initiators are typically present in an amount of about 5% (w/w) or less. Because free-radical initiators do not become chemically a part of the polymers formed, the total amount of initiator is customarily not included when determining the amounts of other ingredients.

The device materials containing a UV/Vis absorber of the present invention optionally also contain a reactive colorant. Suitable reactive blue-light absorbing compounds include those described in U.S. Pat. No. 5,470,932. Blue-light absorbers are typically present in an amount from about 0.01-0.5% (weight).

IOLs constructed of the materials of the present invention can be of any design capable of being rolled or folded into a small cross section that can fit through a relatively smaller incision. For example, the IOLs can be of what is known as a one piece or multipiece design, and comprise optic and haptic components. The optic is that portion which serves as the lens. The haptics are attached to the optic and hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the materials of the present invention are also suitable for use in other ophthalmic devices, such as contact lenses, keratoprostheses, and corneal inlays or rings.

The invention will be further illustrated by the following examples, which are intended to be illustrative, but not limiting.

Example 1

Synthesis of (2-hydroxy-5-methoxy-1,3-phenylene)-dimethanol. In a 2 liter reaction flask equipped with magnetic stirrer was suspended 200 g p-methoxyphenol in 1300 ml water. Formaldehyde solution (335 ml, 37% in water) was added to the stirring solution followed by 55.8 g calcium oxide. The reaction mixture was covered in aluminum foil and allowed to stand at ambient temperature for 10 days. The solid was filtered and then suspended in 1 L deionized water. 130 ml glacial acetic acid was added to the stirring suspension at ambient temperature. The off-white solid was filtered, rinsed with hexane, and then dried under high vacuum for 72 hours to afford 118.9 g (37.8%). $^1$H NMR (DMF-d$_7$) delta: 3.75 (s, 3H, OCH$_3$), 4.73 (s, 4H, CH$_2$O), 5.39 (bs, 2H, CH$_2$O<u>H</u>), 6.85 (s, 2H, Ar—H). $^{13}$C NMR (DMF-d7) delta: 55.12

(1C, OCH$_3$), 59.84 (2C, CH$_2$OH), 111.18 (2C, Ar—CH), 129.51 (2C, Ar—CCH$_2$), 146.30 (1C, Ar—COH), 152.95 (1C, Ar—COCH$_3$).

Example 2

Synthesis of 2-(hydroxymethyl)-4-methoxy-6-((2-nitro-4-(trifluoro-methyl)-phenyl)diazenyl)-phenol. In a 500 ml round bottom flask equipped with a magnetic stirrer was added 19.9 g 2-nitro-4-(trifluoromethyl)-aniline (96.5 mmol) (Aldrich, Milwaukee, Wis.), 41 ml concentrated HCl (aq), 100 ml deionized water, 100 ml ethanol, and 80 ml THF. The suspension was stirred for 30 minutes and 7.07 g sodium nitrite (102 mmol) in 30 ml water was added dropwise over 60 minutes while keeping the reaction mixture at 0° C. The reaction mixture was stirred for an additional 1 hour. 300 mg Sulfamic acid was added to destroy excess nitrite. The mixture was filtered to remove undissolved solids. The filtered diazonium mixture along with a solution of sodium hydroxide (15.1 g in 100 ml water) were added dropwise to a solution containing 19.7 g (2-hydroxy-5-methoxy-1,3-phenylene) dimethanol (107 mmol), 4.3 sodium hydroxide, 200 ml deionized water, and 50 ml THF at 0° C. The reaction mixture was allowed to stir at 0° C. for 1 hour and room temperature for 4 hours. The mixture was poured into 3 liters water. The mixture was acidified to pH 3-4. The dark crude product was filtered and washed with several liters of water to generate a dark solid which was dried under high vacuum at 55° C. for 72 hours to give 15.2 g (42% yield) product.

Synthesis of 2-(hydroxymethyl)-4-methoxy-6-(5-(trifluoromethyl)-2H-benzo[d][1,2,3]triazol-2-yl)phenol. In a 250 ml round bottom flask equipped with a magnetic stirrer was added 7.70 g (20.7 mmol) 2-(hydroxymethyl)-4-methoxy-6-((2-nitro-4-(trifluoromethyl)phenyl)diazenyl)-phenol from Example 2 part 1, 25 ml deionized water, 1.85 g sodium hydroxide, and 80 ml 1-propanol. The mixture was heated to 80° C. and 6.55 g (60.6 mmol) formamidine sulfinic acid (Aldrich) was added slowly and concurrently with a solution of 3.0 g NaOH in 50 ml deionized water. The reaction mixture was heated at 80° C. for 2 hours. The reaction mixture was cooled at −20° C. for 2 hours and filtered. The solid was dissolved in 2.5 L deionized water containing 4 grams NaOH. The pH was adjusted to 2.0 using 1 N HCl. The resultant solid was filtered, washed with ample amounts of deionized water, filtered and dried to give 2.2 g (31%) of a yellow solid. $^1$H NMR (CDCl$_3$) delta: 11.03 (s, 1H, Ar—OH), 8.30 (s, 1H, Ar—H benzotriazole 4-position), 8.07 (d, 1H, Ar—H benzotriazole 6-position), 7.88 (s, 1H, Ar—H phenol), 7.69 (d, 1H, Ar—H benzotriazole), 7.08 (s, 1H, Ar—H phenol), 4.84 (s, 2H, Ar—CH$_2$), 3.90 (s, 3H, Ar—OCH$_3$).

Example 3

Compound WL-1

Synthesis of 2-hydroxy-5-methoxy-3-(5-(trifluoromethyl)-2H-benzo[d][1,2,3]triazol-2-yl)benzyl methacrylate. In a 250 ml round bottom flask equipped with a magnetic stirrer and nitrogen inlet was dissolved 1.15 g (3.39 mmol) 2-(hydroxymethyl)-4-methoxy-6-(5-(trifluoromethyl)-2H-benzo[d][1,2,3]triazol-2-yl)phenol in 50 ml anhydrous THF containing BHT inhibitor (Aldrich). Triethylamine (1.4 ml, 11 mmol) was added and the mixture was cooled to −10° C. Methacryloyl chloride (0.436 g, 4.17 mmol) was added dropwise and the mixture was stirred for 1 hr at −10° C. followed by 20 hours at ambient temperature. The solid was filtered and rinsed with 100 ml diethyl ether. The filtrate was poured into 100 ml diethyl ether and washed with 0.5 N HCl and water. The organic layer was dried with magnesium sulfate, filtered, and then concentrated via rotary evaporation to give the desired product as a dark yellow oil which was recrystallized in methanol to give 0.35 g product (25%). [M+H$^+$]=408.1. $^1$H NMR (CDCl$_3$) delta: 10.97 (s, 1H, Ar—OH), 8.30 (s, 1H, Ar—H benzotriazole), 8.07 (d, 1H, Ar—H benzotriazole), 7.91 (s, 1H, Ar—H phenol), 7.69 (d, 1H, Ar—H benzotriazole), 7.10 (s, 1H, Ar—H phenol), 6.21 (s, 1H, C=C—H trans), 5.62 (s, 1H, C=C—H cis), 5.40 (s, 2H, Ar—CH$_2$), 3.90 (s, 3H, Ar—OCH$_3$), 2.01 (s, 3H, C=C—CH$_3$). Elemental analysis: calculated % C (56.02), % H (3.96), % N (10.32), % F (13.99). found % C (56.11), % H (3.96), % N (10.24), % F (14.37).

Compound WL-1

Example 4

Synthesis of 2-((4-fluoro-2-nitrophenyl)diazenyl)-6-(hydroxymethyl)-4-methoxyphenol. In a 500 ml round bottom flask equipped with a magnetic stirrer was added 25.1 g (161 mmol) 4-fluoro-2-nitroaniline (Aldrich), HCl (aq) (J. T. Baker), 100 ml deionized water, and 100 ml absolute ethanol. The suspension was cooled to 0° C. 11.8 g (171 mmol) Sodium nitrite (Sigma-Aldrich) in 50 ml water was added dropwise over 60 minutes while keeping the reaction mixture at 0° C. The reaction mixture was stirred for an additional 1 hour. 420 mg sulfamic acid (Aldrich) was added and the reaction mixture was stirred for an additional 30 minutes and then filtered. In a 1 liter round bottom flask was combined 32.5 g (176 mmol) (2-hydroxy-5-methoxy-1,3-phenylene) dimethanol, 200 ml deionized water, and 200 ml ethanol. 32.3 g (807 mmol) NaOH (Aldrich) was dissolved in 100 ml water and approximately one-fourth of this was added to the solution containing the phenol derivative at 0° C. The diazonium salt solution and remaining sodium hydroxide solution were added dropwise to the reaction mixture at 0° C. over a 1 hour period and then allowed to stir for an additional 1 hour at 0° C. and 3 hours at ambient temperature. The reaction mixture was poured into 3 liters water and the pH was adjusted to 4 using 1N HCl. The solid was collected by filtration, washed with several liters of water, and vacuum dried (0.1 mm Hg) at 55° C. for 72 hours using P$_2$O$_5$ as drying agent to afford 29.9 g (68%) of a dark solid which was used in the next step without further purification.

Synthesis of 2-(5-fluoro-2H-benzo[d][1,2,3]triazol-2-yl)-6-(hydroxy-methyl)-4-methoxyphenol. In a 500 ml round bottom flask equipped with a magnetic stirrer, liquid addition funnel, powder addition funnel, and nitrogen inlet was added 2-((4-fluoro-2-nitrophenyl)diazenyl)-6-(hydroxymethyl)-4-methoxyphenol and 200 ml ethanol. NaOH (21.7 g, 542 mmol) pellets (97+%, A.C.S. reagent, Aldrich) were dissolved in 100 ml deionized water and approximately one-fourth of the solution was added dropwise to the reaction mixture. The mixture was subsequently heated to 80° C. and 29.3 g (271 mmol) formamidinesulfinic acid (Aldrich) and the remaining sodium hydroxide solution were concurrently added to the reaction mixture over 30 minutes. The mixture was stirred at 80° C. for 3 hours and the contents were then poured into 3 L deionized water and acidified to pH 4 using 1N HCl. The solid was collected by filtration, suspended in 300 ml methanol, and stirred for 30 minutes while cooling to below −20° C. The solid was collected by filtration and then suspended in 300 ml ethanol, cooled again to below 20° C., filtered, and then dried to afford 7.8 g (30%) of a yellow solid, which was used in the next esterification step.

Example 5

Compound WL-2

Synthesis of 3-(5-fluoro-2H-benzo[d][1,2,3]triazol-2-yl)-2-hydroxy-5-methoxybenzyl methacrylate. The esterification was carried out using the product. In a 250 ml round bottom flask equipped with a magnetic stirrer and nitrogen inlet was dissolved 5.06 g (17.5 mmol) 2-(5-fluoro-2H-benzo[d][1,2,3]triazol-2-yl)-6-(hydroxymethyl)-4-methoxyphenol in 60 ml anhydrous THF. Triethylamine (8.7 ml, 62 mmol)) was added and the mixture was cooled to −10-0° C. Methacryloyl chloride (2.26 g, 21.6 mmol) was added dropwise and the mixture was stirred for 1 hr at −10° C. followed by 20 hours at ambient temperature. The salts were filtered and rinsed with 100 ml THF (≧99.9%, anhydrous containing inhibitor, Aldrich). Diethyl ether (100 ml) was added to the filtrate, which was washed with 1N HCl and water, dried over magnesium sulfate, filtered, and concentrated by rotary evaporation to give the desired product, which was recrystallized in ethanol to give 2.5 g (40%) of a yellow solid. $^1$H NMR (CDCl$_3$) delta: 11.03 (s, 1H, phenol OH), 7.94 (m, 1H, Ar—H benzotriazole ring), 7.87 (s, 1H, Ar—H phenol ring), 7.53 (m, 1H, Ar—H benzotriazole ring), 7.29 (m, 1H, Ar—H benzotriazole ring), 7.05 (s, 1H, Ar—H phenol ring), 6.21 (s, 1H, C=C—H trans), 5.61 (s, 1H, C=C—H cis), 5.39 (s, 2H, Ar—CH$_2$), 3.89 (s, 3H, Ar—OCH$_3$), 2.01 (s, 3H, C=C—CH$_3$).

WL-2

Example 6

Synthesis of 2-(hydroxymethyl)-4-methoxy-6-((2-nitrophenyl)-diazenyl)-phenol. In a 500 ml round bottom flask equipped with a magnetic stirrer was added 19.9 g (144 mmol) 2-nitroaniline (Aldrich), HCl (aq), 100 ml deionized water, and 100 ml EtOH. The mixture was cooled to 0° C. and 10.6 g (153 mmol) sodium nitrite in 50 ml water was added dropwise over 60 minutes while keeping the reaction mixture between −10-0° C. The reaction mixture was stirred for an additional 1 hour. 300 mg sulfamic acid was added to destroy excess nitrite and the mixture was stirred for an additional 20 minutes. The solids were filtered and the filtrate containing the diazonium salt was set aside and kept cold at −10° C. NaOH (29.3 g, 731 mmol) was dissolved in 100 ml water and approximately one-fourth was added to a solution of (2-hydroxy-5-methoxy-1,3-phenylene)dimethanol in 100 ml deionized water and 200 ml ethanol. The diazonium salt mixture and remaining sodium hydroxide solution were added to the reaction mixture containing the phenol derivative over a 1 hour period at 0° C. The reaction mixture was allowed to stir at 0° C. for 1 hour and ambient temperature for 3 hours. The contents were poured into 3 liters water and the pH was adjusted to 6 using 1N HCl. The resultant solid was washed with several liters of water and then dried at 55° C. for 40 hours using P$_2$O$_5$ as drying agent to afford 24.4 g (55.8%) of a dark solid which was used in the next step without further purification.

Synthesis of 2-(2H-benzo[d][1,2,3]triazol-2-yl)-6-(hydroxymethyl)-4-methoxyphenol. In a 500 ml round bottom flask equipped with a magnetic stirrer, regular addition funnel, powder addition funnel, and nitrogen inlet was added 23.6 g (77.7 mmol) 2-(hydroxymethyl)-4-methoxy-6-((2-nitrophenyl)diazenyl)phenol and 200 ml ethanol. NaOH (18.8 g, 470 mmol) was dissolved in 100 ml deionized water and approximately one-fourth was added dropwise to the reaction mixture. The mixture was heated to 80° C. and 25.1 g (232 mmol) formamidine sulfinic acid and the remaining sodium hydroxide solution were concurrently added dropwise to the reaction mixture over 30 minutes. The mixture was stirred at 80° C. for 3 hours, poured into 3.5 L water, and then acidified to pH 4 using 1 N HCl. The resultant solid was collected by filtration and worked up as in Example 5 to give a light yellow solid (4.3 g, 20.5%).

Example 7

Compound WL-3

Synthesis of 3-(2H-benzo[d][1,2,3]triazol-2-yl)-2-hydroxy-5-methoxybenzyl methacrylate. In a 250 ml round bottom flask equipped with a magnetic stirrer and nitrogen inlet was dissolved 4.03 g (14.9 mmol) 2-(2H-benzo[d][1,2,3]triazol-2-yl)-6-(hydroxymethyl)-4-methoxyphenol in 50 ml anhydrous THF. Triethylamine (7.4 ml, 53 mmol) was added and the mixture was cooled to −10° C. Methacryloyl chloride (1.99 g, 19.0 mmol) was added dropwise and the mixture was stirred for 1 hr at 0° C. followed by 6 hours at ambient temperature. The mixture was poured into 200 ml diethyl ether and washed with 0.5 N HCl and water. The organic layer was dried with magnesium sulfate, filtered, and concentrated via rotary evaporation to give the desired product as a dark yellow oil which was recrystallized in methanol to give 1.73 g of a light yellow solid (34%). $^1$H NMR (CDCl$_3$) delta: 11.26 (s, 1H, Ar—OH), 7.92 (d, 2H, Ar—H benzotriazole), 7.91 (s, 1H, Ar—H meta to phenol), 7.49 (d, 2H, Ar—H benzotriazole, 5,6-position), 7.05 (s, 1H, Ar—H meta to phenol), 6.21 (s, 1H, C=C—H trans), 5.61 (s, 1H, C=C—H cis), 5.40 (s, 2H, Ar—CH$_2$), 3.90 (s, 3H, Ar—OCH$_3$), 2.01 (s, 3H, C=C—CH$_3$).

Example 8

Synthesis of 2-((5-chloro-2-nitrophenyl)diazenyl)-6-(hydroxymethyl)-4-methoxyphenol. In a 500 ml round bottom flask equipped with a magnetic stirrer was added 30.0 g (174 mmol) 5-chloro-2-nitroaniline (Aldrich), conc. HCl (aq) (J. T. Baker), 100 ml deionized water and 100 ml absolute ethanol. The suspension was cooled to 0° C. and 12.7 g (184 mmol) sodium nitrite in 50 ml water was added dropwise over 30 minutes while keeping the reaction mixture at 0° C. The reaction mixture was stirred for an additional 1 hour. Sulfamic acid (430 mg) was added to destroy excess nitrite and the reaction mixture was stirred for an additional 20 minutes. The solids were filtered and the filtrate containing the diazonium salt was set aside and kept cold at −10° C. NaOH (34.9 g, 873 mmol) was dissolved in 100 ml water and approximately one-fourth was added to a solution of (2-hydroxy-5-methoxy-1,3-phenylene)dimethanol in 100 ml deionized water and 200 ml ethanol. The diazonium salt mixture and remaining sodium hydroxide solution were added to the reaction mixture containing the phenol derivative over a 1 hour period at 0° C. The reaction mixture was allowed to stir at 0° C. for 1 hour and ambient temperature for 2 hours. The contents were poured into 3 liters water and the pH was adjusted to 5 using 1N HCl. The resultant solid was washed with several liters of water and then vacuum dried (0.1 mm Hg) at 55° C. for 40 hours using $P_2O_5$ as drying agent to afford 28.0 g (48%) of a dark solid which was used in the next step without further purification.

Synthesis of 2-(5-chloro-2H-benzo[d][1,2,3]triazol-2-yl)-6-(hydroxymethyl)-4-methoxyphenol. In a 500 ml round bottom flask equipped with a magnetic stirrer, addition funnel, powder addition funnel, and nitrogen inlet was added 27.4 g (81.0 mmol) 2-((5-chloro-2-nitrophenyl)diazenyl)-6-(hydroxymethyl)-4-methoxyphenol and 200 ml ethanol. NaOH (19.7 g, 493 mmol) was dissolved in 100 ml deionized water and approximately one-fourth was added dropwise to the reaction mixture. The mixture was heated to 80° C. and 26.5 g (245 mmol) formamidine sulfinic acid and the remaining sodium hydroxide solution were concurrently added dropwise to the reaction mixture. The mixture was stirred at 80° C. for 2 hours and then poured into 3 L deionized water. The mixture was acidified to pH 3 using 1N HCl and the solid was collected by filtration, rinsed with ample amounts of water, and then worked up as in Example 5 to afford 7.4 g (30%) solid which was used in the next esterification step.

Example 9

Compound WL-4

Synthesis of 3-(5-chloro-2H-benzo[d][1,2,3]triazol-2-yl)-2-hydroxy-5-methoxybenzyl methacrylate. In a 250 ml round bottom flask equipped with a magnetic stirrer and nitrogen inlet was dissolved 3.98 g (13.0 mmol) 2-(5-chloro-2H-benzo[d][1,2,3]triazol-2-yl)-6-(hydroxymethyl)-4-methoxyphenol in 60 ml anhydrous THF. Triethylamine (6.4 ml) was added and the mixture was cooled to −10-0° C. Methacryloyl chloride (1.62 g, 15.5 mmol) was added dropwise and the mixture was stirred for 1 hr at −10-0° C. followed by 20 hours at ambient temperature. The solid was filtered and rinsed with 100 ml diethyl ether. The organic layer was washed with 1 N HCl and water, dried with magnesium sulfate, filtered, and concentrated via rotary evaporation to yield a yellow oil which was recrystallized in ethanol to give 1.73 g (34%) of a light yellow solid. $^1$H NMR (CDCl$_3$) delta: 11.00 (s, 1H, Ar—OH), 7.92 (s, 1H, Ar—H benzotriazole), 7.88 (s, 1H, Ar—H phenol), 7.87 (d, 1H, Ar—H benzotriazole), 7.45 (d, 1H, Ar—H benzotriazole), 7.06 (s, 1H, Ar—H phenol), 6.21 (s, 1H, C═C—H trans), 5.62 (s, 1H, C═C—H cis), 5.38 (s, 2H, Ar—CH$_2$), 3.89 (s, 3H, Ar—OCH$_3$), 2.01 (s, 3H, C═C—CH$_3$).

Example 10

Synthesis of 2-(2-(hydroxymethyl)-4-methoxy-6-(5-methoxy-2H-benzo[d][1,2,3]triazol-2-yl)phenol. In a 500 ml round bottom flask equipped with a magnetic stirrer was added 24.8 g (148 mmol) 4-methoxy-2-nitroaniline (Aldrich), conc. HCl (aq) (J. T. Baker), 150 ml water, and 150 ml absolute ethanol. The mixture was cooled to −20° C. and a solution comprised of 10.8 (156 mmol) sodium nitrite in 40 ml water was added dropwise over 30 minutes. The reaction mixture was stirred for an additional 1 hour and then sulfamic acid (315 mg) was added to destroy excess nitrite. The undissolved solids were filtered and the filtrate containing the diazonium salt was set aside and kept cold at −10° C. NaOH (29.5 g, 739 mmol) was dissolved in 100 ml water and approximately one-fourth was added to a solution comprised of (2-hydroxy-5-methoxy-1,3-phenylene)dimethanol in 100 ml deionized water and 200 ml ethanol. The diazonium salt mixture and remaining sodium hydroxide solution were added to the reaction mixture containing the phenol derivative over a 1 hour period at 0° C. The reaction mixture was allowed to stir at 0° C. for 1 hour and ambient temperature for 3 hours. The contents were poured into 3 liters water and the pH was adjusted to 4.5 using 1N HCl. The resultant solid was filtered, washed with several liters of water, and then vacuum dried (0.1 mm Hg) at 65° C. for 20 hours using $P_2O_5$ as drying agent to afford 33.5 g (68%) of a dark solid which was used in the next step without further purification.

Synthesis of 2-(hydroxymethyl)-4-methoxy-6-(5-methoxy-2H-benzo[d][1,2,3]triazol-2-yl)phenol. In a 500 ml round bottom 3-neck flask equipped with a magnetic stirrer, addition funnel, powder addition funnel, and nitrogen inlet was added 2-(hydroxymethyl)-4-methoxy-6-((4-methoxy-2-nitrophenyl)diazenyl)phenol and 200 ml absolute ethanol (Pharmco Products, Brookfield, Conn.). NaOH pellets, 97% (Aldrich, 16.8 g, 420 mmol) were dissolved in 80 ml deionized water and approximately one-fourth of the solution was added dropwise to the azo mixture. The reaction mixture was heated to 80° C. and 22.6 g (209 mmol) formamidinesulfinic acid (Aldrich) and the remaining NaOH solution were added concurrently to the azo mixture over 0.5 hr. The mixture was heated at 80° C. for 3 hours, poured into 3.5 L water, and acidified to pH 4-5 with conc. HCl (J. T. Baker). The crude product was recrystallizsed from ethanol and then collected and vacuum dried (0.1 mm Hg) at 50° C. for 72 hours to give 7 g (27%) of a light yellow solid.

Example 11

Compound WL-5

Synthesis of 2-hydroxy-5-methoxy-3-(5-methoxy-2H-benzo[d][1,2,3]triazol-2-yl)benzyl methacrylate. In a 100 ml round bottom 3-neck flask equipped with a magnetic stirrer and nitrogen inlet was dissolved 3.24 g (10.8 mmol) 2-(hydroxymethyl)-4-methoxy-6-(5-methoxy-2H-benzo[d][1,2,3]-triazol-2-yl)phenol in 60 ml anhydrous THF. Triethylamine (1.2 ml) was added and the mixture was cooled to −10-0° C. Methacryloyl chloride (1.40 g, 13.4 mmol) was added dropwise and the mixture was stirred for 2 hr at 0° C. followed by 20 hours at ambient temperature. The salts were filtered off and the filtrate was poured into 100 ml diethyl ether and washed with 0.5 N HCl and water. The organic layer was dried with magnesium sulfate, filtered, and concentrated via rotary evaporation to give the desired product as a dark yellow oil which was recrystallized in ethanol to give a light yellow solid. $^1$H NMR (CDCl$_3$) delta: 11.20 (s, 1H, phenol OH), 7.80 (m, 1H, Ar—H benzotriazole), 7.77 (s, 1H, Ar—H phenol), 7.17 (m, 1H, Ar—H benzotriazole), 7.14 (s, 1H, Ar—H phenol), 7.10 (m, 1H, Ar—H benzotriazole), 6.21 (s, 1H, C═C—H trans), 5.61 (s, 1H, C═C—H cis), 5.38 (s, 2H, Ar—C$_{1-12}$), 3.92 (s, 3H, Ar—OCH$_3$, phenol), 3.88 (s, 3H, Ar—OCH$_3$, benzotriazole), 2.01 (s, 3H, C═C—CH$_3$).

WL-5

Example 12

Synthesis of 2-(hydroxymethyl)-4-methoxy-6-((4-methyl-2-nitrophenyl)-diazenyl)phenol. In a 500 ml round bottom flask equipped with a magnetic stirrer was added 24.3 g (160 mmol) 4-methyl-2-nitroaniline, 98% (Aldrich), 67 ml conc. HCl (aq), 100 ml water, and 100 ml absolute ethanol. The mixture was cooled to −10-0° C. and 11.6 g (169 mmol) sodium nitrite in 40 ml water was added dropwise over 30 minutes at −10-0° C. The reaction mixture was stirred for an additional 1 hour and 315 mg sulfamic acid was added to destroy excess nitrite. After an additional 20 minutes of stirring the reaction mixture was filtered and the cold filtrate was set aside. In a 1 L flask was suspended (2-hydroxy-5-methoxy-1,3-phenylene)dimethanol in 200 ml deionized water and 100 ml ethanol. A solution of 32.2 g (805 mmol) sodium hydroxide was prepared and approximately one-fourth was added to the phenol derivative. The phenol derivative was cooled to 0° C. and the diazonium salt mixture and remaining sodium hydroxide solution were added concurrently to the phenol derivative over 1 hour at 0° C. The reaction mixture was stirred at 0° C. for 1 hour and ambient temperature for 3 hours. The mixture was poured into 3 liters water and the pH was adjusted to 4.5 using 1N HCl. The crude product was dried at 65° C. for 20 hours under high vacuum (0.1 mm Hg) using P$_2$O$_5$ as drying agent to afford 30.8 g (61%). The product was used in the next step without further purification.

Synthesis of 2-(hydroxymethyl)-4-methoxy-6-(5-methyl-2H-benzo[d][1,2,3]triazol-2-yl)phenol. In a 500 ml round bottom 3-neck flask equipped with a magnetic stirrer, regular addition funnel, powder addition funnel, and nitrogen inlet was added 30.0 g (94.6 mmol) of the azo compound from part 1 and 200 ml ethanol. NaOH (22.9 g, 573 mmol) was dissolved in 100 ml deionized water and approximately one-fourth of the solution was added dropwise to the reaction mixture. The reaction mixture was heated to 80° C. Formamidinesulfinic acid (30.7 g, 284 mmol) and the remaining sodium hydroxide solution were added concurrently to the azo mixture over 30 minutes. The mixture was heated at 80° C. for 3 hours. The reaction mixture was poured into 3 L water and then acidified to pH 4-5 with 1N HCl. The solid was filtered and then dissolved in 3 L water containing 5 grams NaOH and acidified to pH 2 with 1N HCl. The solid was filtered again and then dried at 55° C. under high vacuum (0.1 mm Hg) for 40 hours to afford 20 g (74%) which was used in the next step without further purification.

Example 13

Compound WL-6

Synthesis of 2-hydroxy-5-methoxy-3-(5-methyl-2H-benzo[d][1,2,3]triazol-2-yl)benzyl methacrylate. In a 100 ml round bottom 3-neck flask equipped with a magnetic stirrer and nitrogen inlet was dissolved 19.5 g (68.3 mmol) 2-(hydroxymethyl)-4-methoxy-6-(5-methyl-2H-benzo[d][1,2,3]triazol-2-yl)phenol in 200 ml anhydrous THF. Triethylamine (34 ml, 240 mmol) was added and the mixture was cooled to −10° C. Methacryloyl chloride (8.55 g, 81.8 mmol) was added dropwise and the mixture was stirred for 2 hr at 0° C. followed by 20 hours at ambient temperature. The solid was filtered and rinsed with diethyl ether and the filtrate was poured into 100 ml diethyl ether and washed with 0.5 N HCl and water. The organic layer was dried with magnesium sulfate, filtered, and concentrated via rotary evaporation. The crude product was recrystallized in ethanol to give 7.2 g (30%) of a light yellow solid. $^1$H NMR (CDCl$_3$) delta: 11.28 (s, 1H, Ar—OH), 7.89 (s, 1H, Ar—H benzotriazole 4-position), 7.79 (d, 1H, Ar—H benzotriazole 6-position), 7.66 (s, 1H, Ar—H phenol 6-position), 7.26 (d, 1H, Ar—H benzotriazole 7-position), 7.03 (s, 1H, Ar—H phenol 4-position), 6.21 (s, 1H, C═C—H trans), 5.61 (s, 1H, C═C—H cis), 5.39 (s, 2H, Ar—CH$_2$), 3.89 (s, 3H, Ar—OCH$_3$), 2.54 (s, 3H, Ar—CH$_3$), 2.01 (s, 3H, C═C—CH$_3$).

WL-6

Example 14

Synthesis of 2-(hydroxymethyl)-4-methyl-6-((2-nitro-4-(trifluoromethyl)-phenyl)-diazenyl)phenol. In a 500 ml round bottom flask equipped with a magnetic stirrer was combined 26.0 g (126 mmol) 2-nitro-4-(trifluoromethyl)-aniline, 53 ml conc. HCl, 100 ml deionized water, and 150 ml ethanol. The mixture was cooled to 0° C. and sodium nitrite in 30 ml water was added dropwise over 60 minutes. The reaction mixture was stirred for an additional 1 hour and 300 mg sulfamic acid was added to destroy the excess nitrite. The solids were filtered and the cold filtrate was set aside. In a 1 liter flask was suspended (2-hydroxy-5-methoxy-1,3-phenylene)dimethanol in 200 ml deionized water and 100 ml ethanol. Approximately one-fourth of a solution of sodium hydroxide (25.4 g, 635 mmol) in 100 ml water was added to the phenolic mixture at 0° C. The diazonium salt mixture and remaining sodium hydroxide solution were added concurrently to the phenolic mixture over 1 hour. The reaction mixture was allowed to stir at 0° C. for 1 hour and room temperature for 4 hours. The mixture was poured in 3 liters water and the pH adjusted to 3-4 using 1N HCl. The solid was filtered and washed with ample amounts of water and then vacuum dried (0.1 mm Hg) at 55° C. for 40 hours to give 27.4 g (76%) of a red solid.

Synthesis of 2-(hydroxymethyl)-4-methyl-6-(5-(trifluoromethyl)-2H-benzo[d][1,2,3]triazol-2-yl)phenol. In a 1 L round bottom flask equipped with a magnetic stirrer, addition funnel, powder addition funnel, and nitrogen inlet was added 26.0 g (73.2 mmol) 2-(hydroxymethyl)-4-methyl-6-((2-nitro-4-(trifluoromethyl)phenyl)-diazenyl)phenol and 300 ml ethanol. Sodium hydroxide (17.6 g, 441 mmol) was dissolved in 100 ml deionized water and approximately one fourth was added dropwise to the azo mixture. The reaction mixture was heated to 80° C. and 23.9 g (221 mmol) formamidinesulfinic acid and the remaining sodium hydroxide solution were added to the azo mixture over 30 minutes. The reaction mixture was heated at 80° C. for 3 hours, poured in 3 L deionized water, and acidified to pH 4 using 1N HCl. The solid was collected by vacuum filtration, washed with ample amounts of water, and then dried for 20 hours under vacuum (0.1 mm Hg) at 42° C. to give 18.6 g (79%) of an off white solid.

Example 15

Compound WL-7

Synthesis of 2-hydroxy-5-methyl-3-(5-(trifluoromethyl)-2H-benzo[d][1,2,3]triazol-2-yl)benzyl methacrylate. In a 100 ml round bottom 3-neck flask equipped with a magnetic stirrer and nitrogen inlet was dissolved 3.58 g (11.1 mmol) 2-(hydroxymethyl)-4-methyl-6-(5-(trifluoromethyl)-2H-benzo[d][1,2,3]triazol-2-yl)phenol in 60 ml anhydrous THF. Triethylamine (5.6 ml, 40 mmol) was added and the mixture was cooled to −10° C. Methacryloyl chloride (1.373 g, 13.1 mmol) was added dropwise and the mixture was stirred for 1 hour at −10° C. followed by 20 hours at ambient temperature. The solid was filtered off and rinsed with diethyl ether and the resultant filtrate was poured into 100 ml diethyl ether and washed with 0.5 N HCl and water. The organic layer was dried with magnesium sulfate, filtered, and recrystallized with diethyl ether to give 1.90 g (44%) of a white solid. $^1$H NMR (CDCl$_3$) delta: 11.17 (s, 1H, Ar—OH), 8.29 (s, 1H, Ar—H benzotriazole 4-position), 8.21 (s, 1H, Ar—H phenol 6-position), 8.06 (d, 1H, Ar—H benzotriazole 6-position), 7.69 (d, 1H, Ar—H benzotriazole 7-position), 7.29 (s, 1H, Ar—H phenol 4-position), 6.20 (s, 1H, C=C—H trans), 5.61 (s, 1H, C=C—H cis), 5.39 (s, 2H, Ar—CH$_2$), 2.42 (s, 3H, Ar—CH$_3$), 2.00 (s, 3H, C=C—CH$_3$).

WL-7

Example 16

Figure 1:
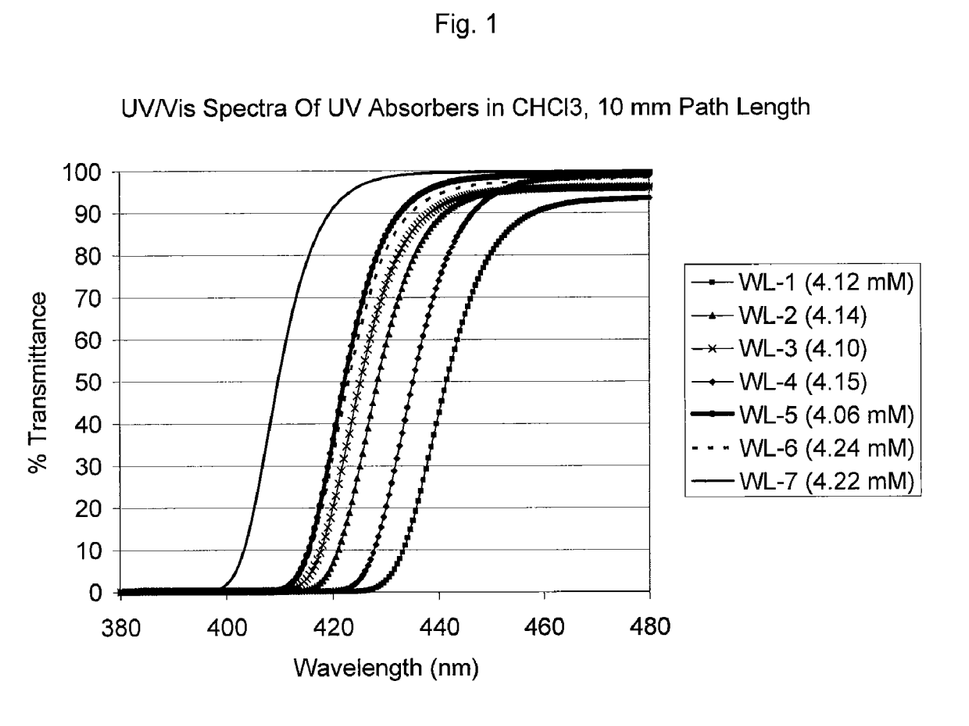
FIG. 1 shows percent transmittance curves for UV/Vis absorber compounds WL-1-WL-7.
Figure 2A:
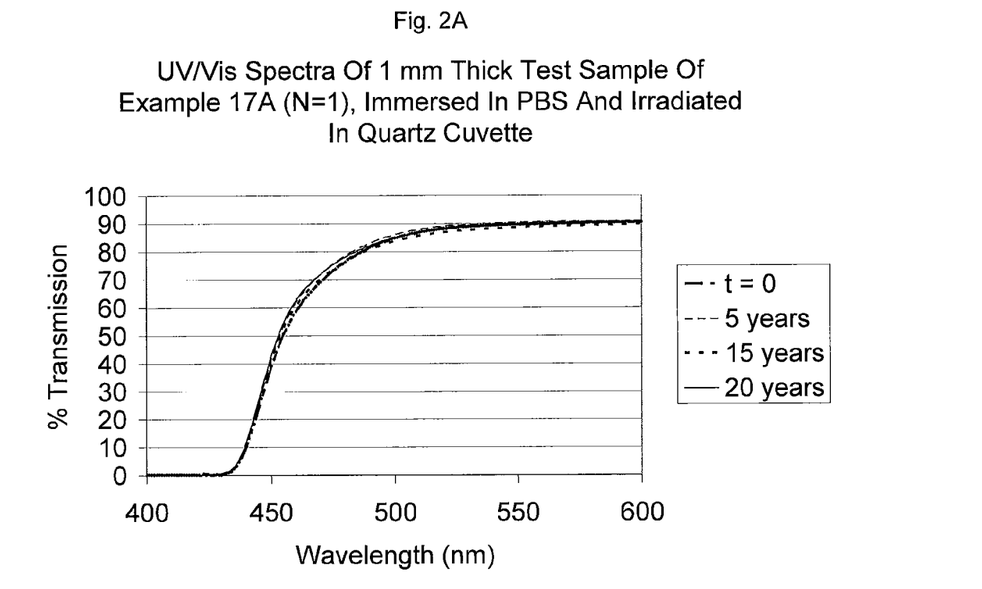
FIGS. 2A-2J show percent transmittance curves for IOL materials containing UV/Vis absorber compounds WL-1-WL-4 that were subjected to photostability testing producing the equivalent of 10 or 20 years of light exposure.
Figure 2B:
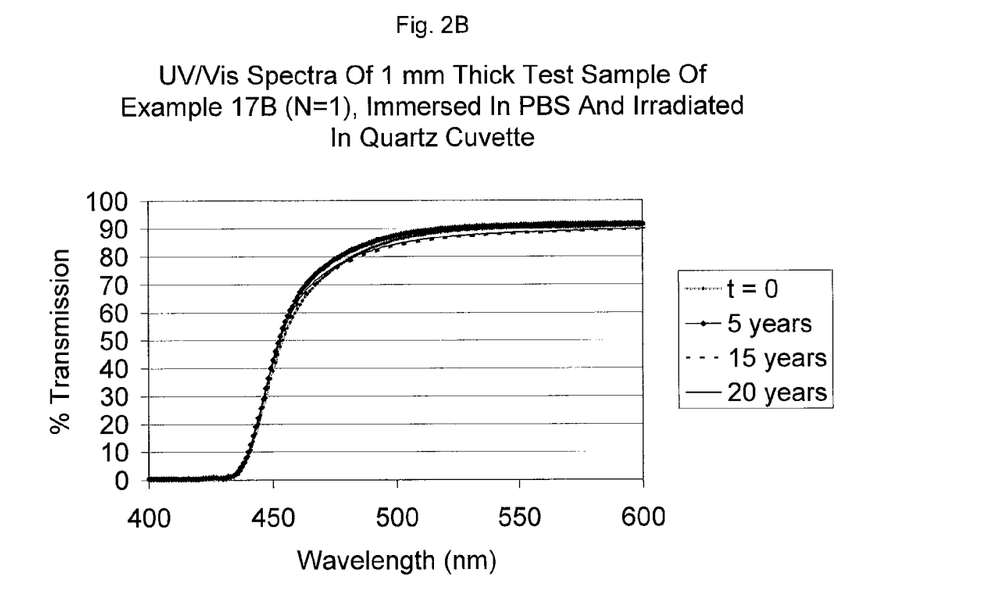
Figure 2C:
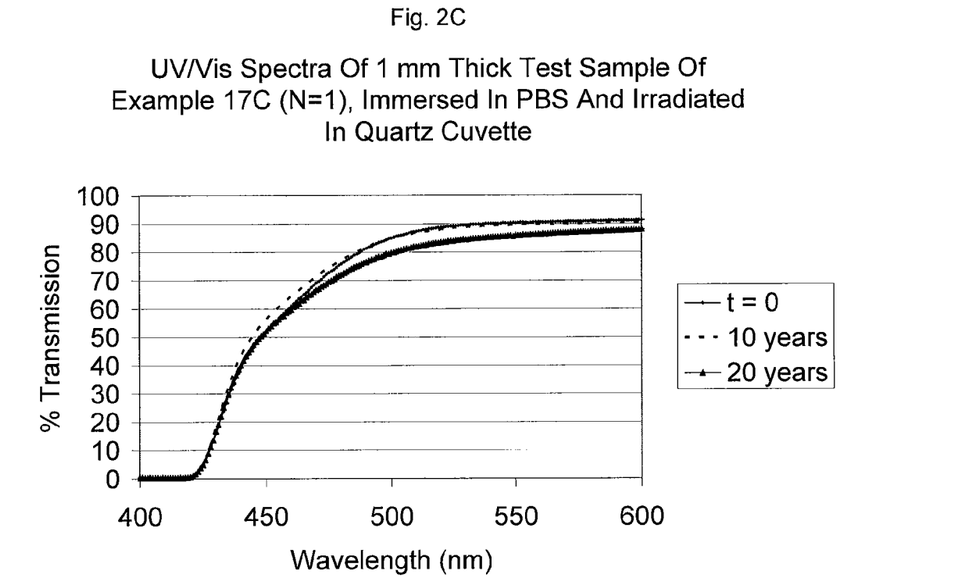
Figure 2D:
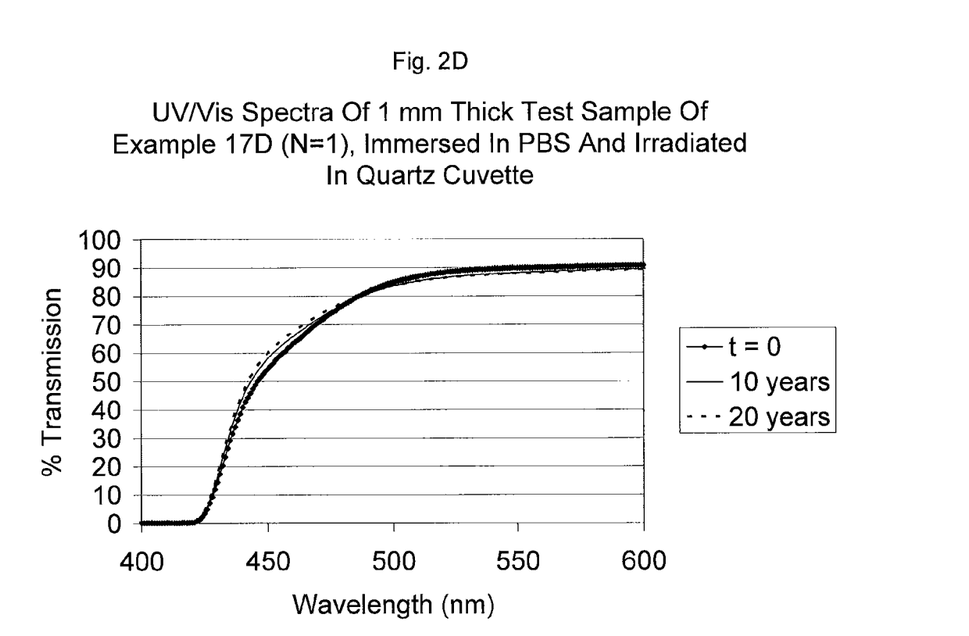
Figure 2E:
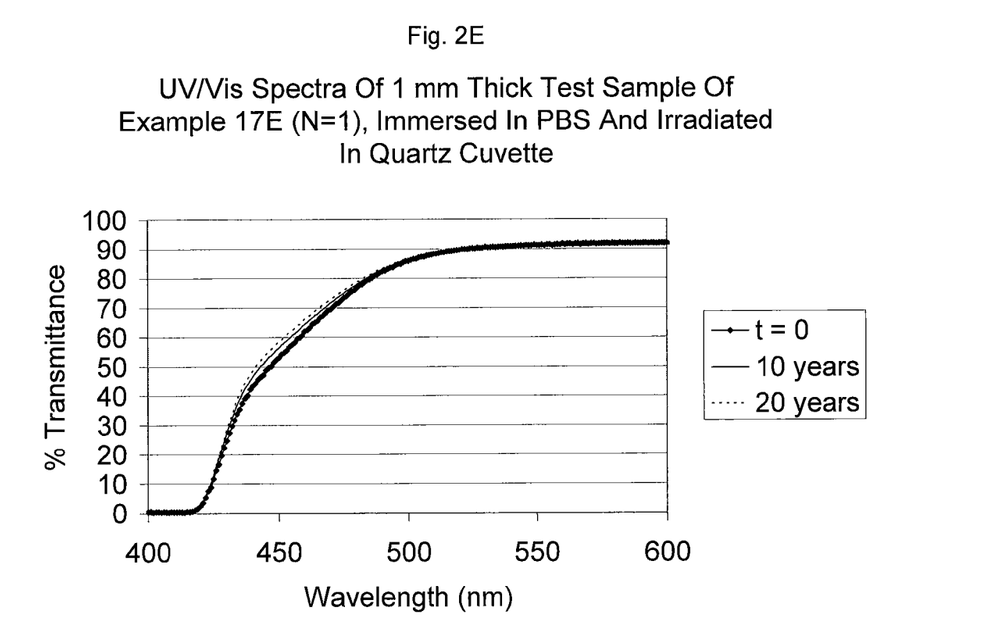
Figure 2F:
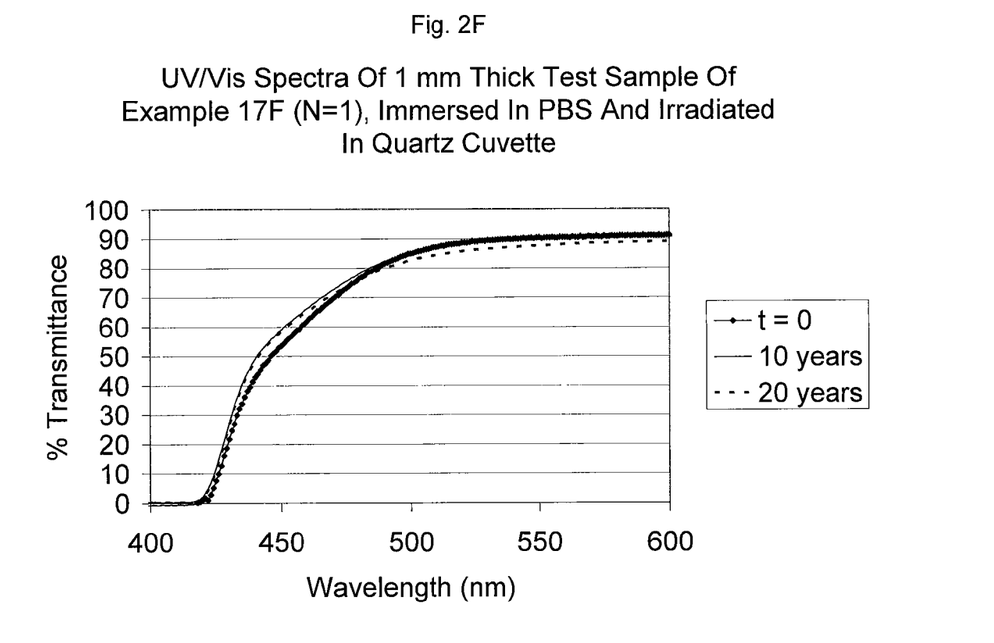
Figure 2G:
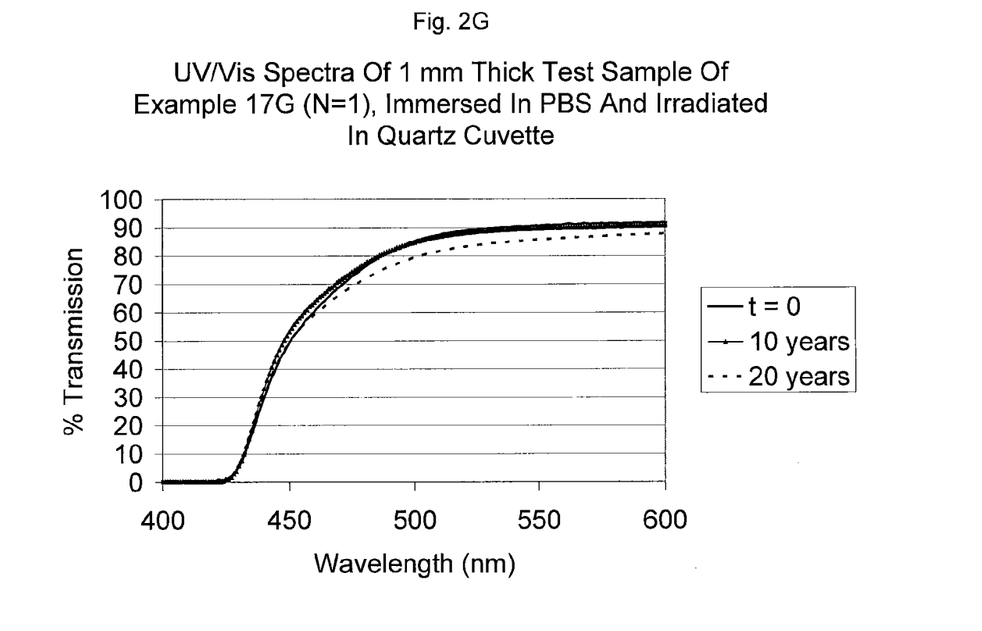
Figure 2H:
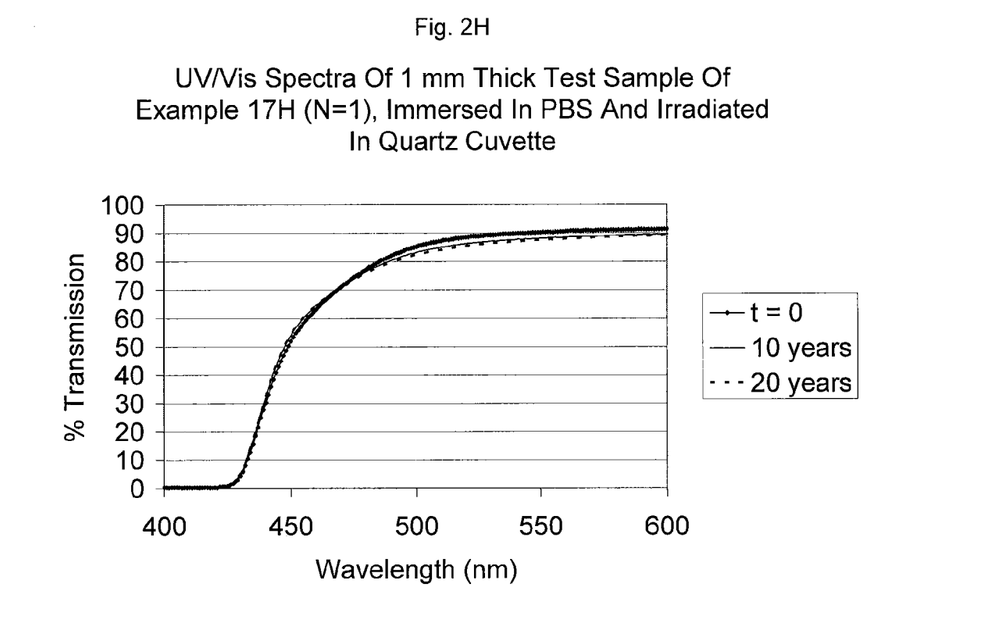
Figure 2I:
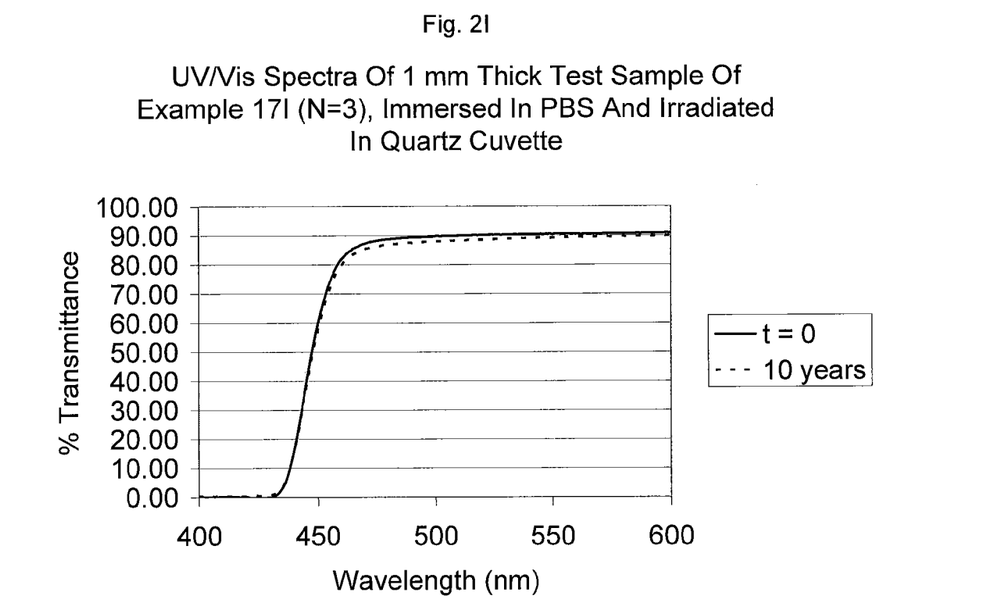
Figure 2J:
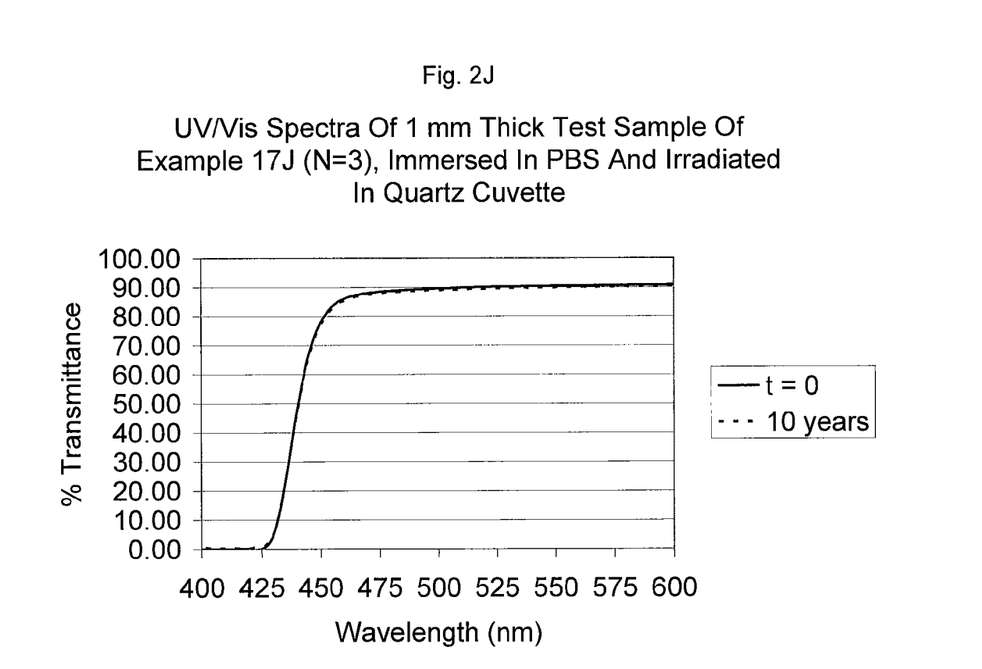

Transmittance curves for Compounds WL-1 through WL-7 were generated by UV/Vis spectroscopy. Each compound was dissolved in chloroform and evaluated in a PerkinElmer Lambda 35 UV/Vis spectrometer. The results are shown in FIG. 1 and the 1% T and 10% T results are shown in Table 1.

TABLE 1

| Compound | Concentration (mM) | Concentration (w/v %) | 1% T wavelength (nm) | 10% T wavelength (nm) |
|---|---|---|---|---|
| WL-1 | 4.12 | 0.168 | 428 | 433 |
| WL-2 | 4.14 | 0.148 | 416 | 421 |
| WL-3 | 4.10 | 0.139 | 413 | 418 |
| WL-4 | 4.15 | 0.155 | 423 | 428 |
| WL-5 | 4.06 | 0.150 | 411 | 416 |
| WL-6 | 4.24 | 0.150 | 411 | 416 |
| WL-7 | 4.22 | 0.165 | 399 | 403 |

Example 17

Acrylic IOL Formulations

Compounds WL-1-WL-4 were formulated in IOL materials as shown in Tables 2-6. All components were vortex mixed in a 30 ml glass vial, degassed with nitrogen, and then syringe filtered using a 0.2 micron Teflon filter into ~1 mm deep rectangular polypropylene molds. Samples were thermally cured at 70° C. for 1 hour and 110° C. for 2 hours and then extracted in acetone at 50° C. for 6 hours with fresh solvent replacement every 90 minutes.

TABLE 2

| | Example (% w/w) | |
|---|---|---|
| Component | 17A | 17B |
| Compound WL-1 (Example 3) | 1.81 | 1.81 |
| N-2-(3-(2-methylphenylazo)-4-hydroxy-phenyl)-ethylmethylacrylamide | 0.021 | 0.021 |
| PEA | 48.8 | — |
| PEMA | 42.9 | — |
| BzA | — | 79.7 |
| BzMA | — | 12.0 |

TABLE 2-continued

| Component | Example (% w/w) 17A | 17B |
|---|---|---|
| Secondary alcohol ethoxylate, methacrylic acid ester | 5.01 | 5.00 |
| BDDA | 1.50 | 1.51 |
| AIBN | 0.56 | 0.59 |

PEA = 2-phenylethyl acrylate
PEMA = 2-phenylethyl methacrylate
BzA = benzyl acrylate
BzMA = benzyl methacrylate
BDDA = 1,4-butanediol diacrylate
Secondary alcohol ethoxylate, methacrylic acid ester = methacrylic acid ester of Tergitol ™ 15-S-30 surfactant (Dow/Union Carbide)
AIBN = 2,2'-Azobis(2-methylpropionitrile)

TABLE 3

| Component | Example (% w/w) 17C | 17D |
|---|---|---|
| Compound WL-2 (Example 5) | 1.81 | 1.81 |
| N-2-(3-(2-methylphenylazo)-4-hydroxy-phenyl)-ethylmethylacrylamide | 0.021 | 0.021 |
| PEA | 48.8 | — |
| PEMA | 42.9 | — |
| BzA | — | 79.7 |
| BzMA | — | 12.0 |
| Secondary alcohol ethoxylate, methacrylic acid ester | 5.01 | 5.00 |
| BDDA | 1.50 | 1.51 |
| AIBN | 0.55 | 0.53 |

TABLE 4

| Component | Example (% w/w) 17E | 17F |
|---|---|---|
| Compound WL-3 (Example 7) | 1.80 | 1.82 |
| N-2-(3-(2-methylphenylazo)-4-hydroxy-phenyl)-ethylmethylacrylamide | 0.021 | 0.021 |
| PEA | 48.8 | — |
| PEMA | 42.9 | — |
| BzA | — | 79.7 |
| BzMA | — | 12.0 |
| Secondary alcohol ethoxylate, methacrylic acid ester | 5.01 | 5.00 |
| BDDA | 1.50 | 1.51 |
| AIBN | 0.50 | 0.52 |

TABLE 5

| Component | Example (% w/w) 17G | 17H |
|---|---|---|
| Compound WL-4 (Example 9) | 1.80 | 1.80 |
| N-2-(3-(2-methylphenylazo)-4-hydroxy-phenyl)-ethylmethylacrylamide | 0.021 | 0.021 |
| PEA | 48.8 | — |
| PEMA | 42.9 | — |
| BzA | — | 79.7 |
| BzMA | — | 12.0 |
| Secondary alcohol ethoxylate, methacrylic acid ester | 5.00 | 5.00 |
| BDDA | 1.50 | 1.50 |
| AIBN | 0.50 | 0.51 |

TABLE 6

| Component | Example (% w/w) 17I | 17J |
|---|---|---|
| Compound WL-1 (Example 3) | 1.67 | — |
| Compound WL-4 (Example 9) | — | 1.53 |
| BzA | 83.7 | 83.9 |
| BzMA | 10.0 | 10.0 |
| PolyPEGMA | 3.02 | 3.03 |
| BDDA | 1.58 | 1.53 |
| AIBN | 0.50 | 0.51 |

PolyPEGMA = Macromonomer of poly(ethylene glycol) monomethyl ether methacrylate (MW = 550), Mn (SEC): 4100 Daltons, Mn (NMR): 3200 Daltons, PDI = 1.50.

Example 18

Photostability

Samples of Formulations 17A, 17B, 17C, 17D, 17E, 17F, 17G, 17H, 17I, and 17J were subject to UV radiation from 300 to 800 nm using an Atlas Suntest CPS+ test chamber (Atlas Electric Devices Company, Chicago, Ill.) utilizing a xenon arc lamp with light intensity of approximately 8-10 mW/cm$^2$ at the height of the test sample. The temperature of the PBS medium was 35° C. UV/Vis spectra from 0.9 mm thick sample sections were collected using a PerkinElmer Lambda 35 UV/Vis spectrometer. Results from light exposure equivalent to 20 years (Examples 17A-17H) or 10 years (Examples 17I and 17J) are shown in FIGS. 2A-2J.

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

I claim:

1. A benzotriazole compound of the formula wherein
$R^1$=H, $CH_3$, $CH_2CH_3$, or $CH_2OH$;
$R^2$=$C_1$-$C_4$ alkoxy; and
$R^3$=H, $CH_3$, $CH_3O$, F, Cl, Br, I, or $CF_3$.

2. A benzotriazole compound of claim 1 wherein
$R^1$=H or $CH_3$;
$R^2$=$C_1$-$C_4$ alkoxy; and
$R^3$=H, $CH_3$, $CH_3O$, F, Cl, or $CF_3$.

3. A benzotriazole compound of claim 2 wherein the compound is selected from the group consisting of:
2-hydroxy-5-methoxy-3-(5-(trifluoromethyl)-2H-benzo[d][1,2,3]triazol-2-yl)benzyl methacrylate;
3-(5-fluoro-2H-benzo[d][1,2,3]triazol-2-yl)-2-hydroxy-5-methoxybenzyl methacrylate;
3-(2H-benzo[d][1,2,3]triazol-2-yl)-2-hydroxy-5-methoxybenzyl methacrylate;
3-(5-chloro-2H-benzo[d][1,2,3]triazol-2-yl)-2-hydroxy-5-methoxybenzyl methacrylate;
2-hydroxy-5-methoxy-3-(5-methoxy-2H-benzo[d][1,2,3]triazol-2-yl)benzyl methacrylate; and
2-hydroxy-5-methoxy-3-(5-methyl-2H-benzo[d][1,2,3]triazol-2-yl)benzyl methacrylate.

4. A benzotriazole compound of claim 3 wherein the compound is 2-hydroxy-5-methoxy-3-(5-(trifluoromethyl)-2H-benzo[d][1,2,3]triazol-2-yl)benzyl methacrylate.

5. A benzotriazole compound of claim 3 wherein the compound is
3-(5-chloro-2H-benzo[d][1,2,3]triazol-2-yl)-2-hydroxy-5-methoxybenzyl methacrylate.

6. An ophthalmic device material comprising a benzotriazole compound of claim 1 and a device-forming monomer selected from the group consisting of acrylic monomers and silicone-containing monomers.

7. The ophthalmic device material of claim 6 wherein the ophthalmic device material comprises from 0.1 to 3% w/w of a benzotriazole compound of claim 1.

8. The ophthalmic device material of claim 7 wherein the ophthalmic device material comprises from 0.2 to 2.5% w/w of a benzotriazole compound of claim 1.

9. The ophthalmic device material of claim 8 wherein the ophthalmic device material comprises from 0.3 to 2% w/w of a benzotriazole compound of claim 1.

10. The ophthalmic device material of claim 6 wherein the ophthalmic device material comprises a device-forming monomer of formula [IV]:

where in formula [IV]:
A is H, $CH_3$, $CH_2CH_3$, or $CH_2OH$;
B is $(CH_2)_m$ or $[O(CH_2)_2]_z$;
C is $(CH_2)_w$;
m is 2-6;
z is 1-10;
Y is nothing, O, S, or NR', provided that if Y is O, S, or NR', then B is $(CH_2)_m$;
R' is H, $CH_3$, $C_{n'}H_{2n'+1}$ wherein n'=1-10, iso-$OC_3H_7$, $C_6H_5$, or $CH_2C_6H_5$;
w is 0-6, provided that m+w≦8; and
D is H, $C_1$-$C_4$ alkyl, $C_1$-$C_4$ alkoxy, $C_6H_5$, $CH_2C_6H_5$ or halogen.

11. The ophthalmic device material of claim 10 wherein in formula [IV]:
A is H or $CH_3$;
B is $(CH_2)_m$;
m is 2-5;
Y is nothing or O;
w is 0-1; and
D is H.

12. The ophthalmic device material of claim 11 wherein the ophthalmic device material comprises a monomer selected from the group consisting of: 2-phenylethyl methacrylate; 4-phenylbutyl methacrylate; 5-phenylpentyl methacrylate; 2-benzyloxyethyl methacrylate; and 3-benzyloxypropyl methacrylate; and their corresponding acrylates.

13. The ophthalmic device material of claim 6 wherein the ophthalmic device material comprises a cross-linking agent.

14. The ophthalmic device material of claim 6 wherein the ophthalmic device material comprises a reactive blue-light absorbing compound.

15. An intraocular lens comprising a benzotriazole compound of claim 1.

16. An intraocular lens comprising a benzotriazole compound of claim 2.

17. An intraocular lens comprising a benzotriazole compound of claim 3.

18. An ophthalmic device comprising the ophthalmic device material of claim 6.

19. The ophthalmic device of claim 18 wherein the ophthalmic device is selected from the group consisting of an intraocular lens; a contact lens; a keratoprosthesis; and a corneal inlay or ring.

* * * * *